United States Patent [19]
Scholin et al.

[11] Patent Number: 5,958,689
[45] Date of Patent: Sep. 28, 1999

[54] DETECTION OF TOXIGENIC MARINE DIATOMS OF THE GENUS PSEUDO-NITZSCHIA

[75] Inventors: Christopher A. Scholin, Monterey, Calif.; Gerard A. Cangelosi; Paul V. Haydock, both of Seattle, Wash.

[73] Assignee: Monterey Bay Aquarium Research Institute, Moss Landing, Calif.

[21] Appl. No.: 08/861,096

[22] Filed: May 21, 1997

Related U.S. Application Data

[60] Provisional application No. 60/018,143, May 22, 1996.

[51] Int. Cl.$^6$ .............. C12Q 1/68; C07H 21/02; C07H 21/04; C12N 15/00
[52] U.S. Cl. .............. 435/6; 536/23.1; 536/24.3; 935/76; 935/77; 935/78
[58] Field of Search .............. 435/6; 536/23.1, 536/24.3; 935/76, 77, 78

[56] References Cited

U.S. PATENT DOCUMENTS

| | | | |
|---|---|---|---|
| 5,212,059 | 5/1993 | Schwartz et al. | 435/6 |
| 5,582,983 | 12/1996 | Anderson et al. | 435/6 |
| 5,595,874 | 1/1997 | Hogan et al. | |
| 5,707,802 | 1/1998 | Sandhu et al. | 435/6 |
| 5,712,095 | 1/1998 | Britschgi et al. | 435/6 |

OTHER PUBLICATIONS

Sommer et al., Nucleic Acids Research 17(6):6749 (1989).
Rijk et al., Nucleic Acids Research 22(17):3495–3501 (1994).
Baroin et al., PNAS 85:3474–3478 (1988).
Steffan et al., Annual Review of Microbiology 45:137–161.
Douglas, Donald J. et al., *Natural Toxins* 2:166–174 (1994).
Scholin, C.A., et al., *Natural Toxins* 2:152–165 (1994).

*Primary Examiner*—W. Gary Jones
*Assistant Examiner*—Ethan Whisenant
*Attorney, Agent, or Firm*—Townsend and Townsend and Crew LLP

[57] ABSTRACT

The present invention provides compositions, methods, and kits for detecting species of *Pseudo-nitzschia* from a marine sample. Oligonucleotide probes for rRNA hypervariable regions of the *Psuedo-nitzschia* species: *P. australis, P. pungens, P. multiseries, P. pseudodelicatissima, P. heimii, P. fraudulenta, P. delicatissima,* and *P. americana* are provided as well as a oligonucleotide probe for a conserved region of ribosomal RNA from *Pseudo-nitzschia*.

23 Claims, No Drawings

US 5,958,689

DETECTION OF TOXIGENIC MARINE DIATOMS OF THE GENUS PSEUDO-NITZSCHIA

This application claims benefit of Provisional Application Ser. No. 60/018,143, filed May 22, 1996.

FIELD OF THE INVENTION

The present invention relates, in general, to compositions, methods and diagnostic kits useful for the detection of species of the marine algae *Pseudo-nitzschia* from a marine sample.

BACKGROUND OF THE INVENTION

Amnesic shellfish poisoning was first recognized in 1987 at Prince Edward Island, Canada, after several people died and over one hundred became ill following the consumption of blue mussels (Bates et al., *Canadian Journal of Fisheries and Aquatic Science* 46:1203–1215 (1989); Perl et al., *N. Eng. J. Med.* 322:1775–1778 (1990)). The causative agent was identified as domoic acid, a naturally occurring neuroexcitatory amino acid produced by the pennate diatom *Pseudonitzschia pungens* (Grunow) Hasle forma multiseries (Hasle) Hasle (Subba Rao et al., *Can. J. Fish Aquatic Sci* 45:2076–2079 (1988); Bates et al., *Canadian Journal of Fisheries and Aquatic Science* 46:1203–1215 (1989); Douglas, et al., *Can. J. Fish. Aquatic Sci.* 49:85–90 (1992); Hasle, G. R., *Nova Hedwigia, Beiheft* 106:315–321 (1993)). Mussels that fed upon a bloom of this diatom concentrated the associated toxin, serving as a vector for human poisonings. Prior to this event, domoic acid was not considered a public health concern nor was it associated with blooms of diatoms. In following years, reports of toxic Pseudonitzschia blooms, as well as findings of domoic acid in shellfish, became more prevalent, but were restricted to eastern North America (Subba Rao et al., *Can. J. Fish Aquatic Sci* 45:2076–2079 (1988); Shumway, S. E., *World Aquaculture* 20:65–74 (1989); Martin et al., *Mar. Ecol. Prog. Ser.* 67:177–182 (1990). However, in 1991, the death of brown pelicans and cormorants in the vicinity of Santa Cruz, California (Monterey Bay), subsequent shellfish bans in Oregon and Washington, and a limited number of minor, human poisonings were also linked to this toxin, being the first recorded domoic acid outbreak in western North America (Anonymous, *Communicable Diseases Summary, Oregon Health Division, Portland* 40:1–2 (1991); Work et al., *Toxin Marine Phytoplankton* (Ed. by Graneli, et al.), pp. 643–649 (1993)). The pelican and cormorant mortalities coincided with a massive bloom of *P. australis* Frenguelli, the associated toxin of which was concentrated by feeding anchovies (Buck et al., *Marine Ecological Progress Series* 84:293–302 (1992); Fritz et al., *Journal of Phycology* 28:439–442 (1992); Garrison et al., *Journal of Phycology* 28:604–607 (1992); Work et al., *Toxin Marine Phytoplankton* (Ed. by Graneli, et al.), pp. 643–649 (1993)).

Domoic acid poisonings in eastern and western North America have drawn considerable attention to the potential for future outbreaks (Wood, et al. (eds.), *Domoic Acid, Final Report of the Workshop, Oregon Institute of Marine Biology*, Feb. 21–23, 1992 (1993)). In addition, there are concerns of the toxin's transfer through the food web, bio-accumulation and possible bio-transformation. The global distribution of Pseudonitzschia spp. shown to produce domoic acid also suggests the problem could be widespread (Hallegraeff, G. M., *Phycologia* 32:79–99 (1993); Villac et al., *J. Shellish Res.* 12:457–65 (1993); Villac et al., *Hydrobiologia* 267/ 270:213–24 (1993)). Not surprisingly, the study of Pseudonitzschia species has intensified, a trend that reflects both the public's and scientific communities' concerns over the safety of sea food and human's potential impact on the coastal environment.

Toxic Pseudonitzschia species can be difficult to identify, and in most cases require electron microscopy and an expert taxonomist for unambiguous classification. Consequently, detection and enumeration of such species in field samples is both challenging and labor intensive, especially when large numbers of samples are to be processed on a routine basis. In turn, "early warning" of potential domoic acid outbreaks may be compromised, particularly in areas where bloom cycles of Pseudonitzschia are poorly characterized, or in regions that harbor multiple, toxic and non-toxic Pseudonitzschia species, or when expert taxonomists are unable to immediately examine suspect samples.

In a step towards circumventing these problems, Douglas et al., *Natural Toxins* 2:166–174 (1994) and Scholin et al., *Natural Toxins* 2:152–165 (1994) showed that *Pseudo-nitzschia* species harbour unique ribosomal RNA sequences, suggesting a genetic basis from which one might delineate potentially toxic from non-toxic congeners. Ribosomal RNA (rRNA) sequences have been used since the late 1970s to define evolutionary and taxonomic relationships of numerous life forms (Woese et al., *Proceedings of the National Academy of Science, U.S.A.* 74:5088–5090 (1977); De Rijk et al., *Nucleic Acids Research* 22:3495–3501 (1994); Van de Peer et al. *Nucleic Acids Research* 22:3488–3494 (1994). Comparison of rRNA sequences from different organisms has shown that the molecule is comprised of a mosaic of conserved and variable domains. Ribosomal RNAs also occur at high copy number per cell, thus providing a naturally amplified hybridization target per cell (Vaheri et al. (eds.), *Rapid Methods and Automation in Microbiology and Immunology*, Springer-Verlag, NY (1991)).

In view of the potential contamination of sea food by toxigenic algal blooms, what is needed in the art is a means to rapidly detect and quantify *Pseudo-nitzschia* species from a marine sample. In particular, what is needed is an assay for single or multiple species of the genus *Pseudo-nitzschia* by detecting species-specific regions of rRNA accessible under non-denaturing conditions. The present invention provides these and other advantages.

SUMMARY OF THE INVENTION

In one aspect, the present invention is directed to a composition of polynucleotide probes for the detection of *Pseudo-nitzschia* species from a marine sample. The probes comprise a segment of nucleic acid capable of selectively hybridizing, under selective hybridizing conditions, to a hypervariable region of ribosomal RNA selected from the group consisting of:

for *P. australis*
  5'-CCGCCUGGUGGAGUGAGUCAUUU-3' (SEQ ID NO:1)
  5'-CCUGGUGGAGUGAGUCAUUU-3' (SEQ ID NO:2)
for *P. pungens*
  5'-CCGCCUGGUAAAGUGAGUCA-3' (SEQ ID NO:3)
  5'-UGGUAAAGUGAGUCAU-3' (SEQ ID NO:4)
  5'-GGCCUGGGCGCUGUGAGCUU-3' (SEQ ID NO:5)
for *P. multiseries*
  5'-CCUGGCAGAGUGAGUCAUUU-3' (SEQ ID NO:6)
  5'-UGGCAGAGUGAGUCAU-3' (SEQ ID NO:7)
for *P. multiseries* and *P. pseudodelicatissima*

5'-UGGCUUGGGCGCUGUGGGCU-3' (SEQ ID NO:8)
5'-GGCUUGGGCGCUGUGGGCUU-3' (SEQ ID NO:9)
for *P. heimii*

5'-UCUGGUAGAAUGAGUCAUGG-3' (SEQ ID NO:10)

5'-UAUGUUCAUAUUUCCCUUG-3' (SEQ ID NO:11)

5'-UGUGGGCGCUGUGGAUA-3' (SEQ NO:12)
for *P. fraudulenta*

5'-CCUGGUAGAAUGAGUCUUU-3' (SEQ ID NO:13)
for *P. delicatissima*

5'-UGGUAGAGUGAGUCU-3' (SEQ ID NO:14)
for *P. americana*

5'-UGGCUGAAUGAGUCAU-3' (SEQ ID NO:15)
and combinations thereof. Any additional nucleic acid sequences covalently bound to the segment of nucleic acid of the probe do not hybridize, under the selective hybridization conditions, to nucleic acids of *Pseudo-nitzschia* species in the sample.

In another aspect of the invention, a polynucleotide probe is provided for the detection of *Pseudo-nitzschia* species from a marine sample. The probe comprises a segment of nucleic acid capable of selectively hybridizing, under selective hybridizing conditions, to a conserved region of ribosomal RNA, where the conserved region is: 5'-GATGCAAAGAACUUUGAAAAGAGAGUUAAA-GAG-3' (SEQ ID NO:16). Any additional nucleic acid sequences covalently bound to the segment of nucleic acid does not hybridize under the selective conditions to nucleic acids of *Pseudo-nitzschia* species in the sample.

In addition to composition claims, methods are disclosed for the detection of *Pseudo-nitzschia* species from a marine sample. These methods comprise the steps of: permeabilizing the species of *Pseudo-nitzschia* to be assayed for to expose the ribosomal RNA; contacting the exposed ribosomal RNA, under hybridizing conditions, with polynucleotide probes capable of selectively hybridizing to the hypervariable regions of the ribosomal RNA of at least one species of *Psuedo-nitzschia*; and detecting hybridization complexes as an indication of the presence of the microbial cell in the sample. More specifically, there is disclosed herein the above method, where the *Pseudo-nitzschia* detected is selected from the list of *Pseudo-nitzschia* species including: *P. australis, P. pungens, P. multiseries, P. pseudodelicatissima, P. heimii, P. fraudulenta, P. delicatissima, P. americana* or combinations thereof.

In addition to compositions and methods, there are disclosed herein diagnostic kits for use in determining the presence of *Pseudo-nitzschia* which comprise a synthetic oligonucleotide probe complementary to the aforementioned hypervariable or conserved regions of the ribosomal RNA of a *Psuedo-nitzschia* species from a marine sample.

The present invention has utility in providing an easy, sensitive, and specific test for potentially toxigenic marine algae which may contaminate sea food.

DESCRIPTION OF THE PREFERRED EMBODIMENTS

The present invention is directed to compositions of oligonucleotide probes for the detection of species of *Pseudo-nitzschia* from a marine sample, wherein the probes comprise a segment of nucleic acid capable of selectively hybridizing, under selective hybridizing conditions, to regions of the large subunit (LSU) of ribosomal RNA (rRNA) from *Psuedo-nitzschia* species with the provision that any additional nucleotides covalently bound to the segment do not hybridize under the selective conditions to nucleic acids of *Pseudo-nitzschia* species from the marine sample. Methods of detection and diagnostic kits for the assay of *Psuedo-nitzschia* species are also disclosed.

The probes of the present invention are able to specifically hybridize to portions of the rRNA, or rRNA coding regions of genomic DNA, which varies (i.e., is hypervariable) amongst species of the genus *Pseudo-nitzschia*. Hypervariability permits ready detection and identification of species of *Psuedo-nitzschia* without cross-reacting with other probe accessible nucleic acids of *Pseudo-nitzschia* species from the sample. Compositions of oligonucleotide probes directed to conserved regions of *Psuedo-nitzschia* rRNA are also described, where the probes can be utilized as specific probes for rRNA or the corresponding genomic sequence. The disclosed probes are able to hybridize to regions of rRNA without the requirement of heat denaturation. The present invention therefore provides a convenient and sensitive means to assay for potentially toxigenic species of *Pseudo-nitzschia*.

Definitions

Unless defined otherwise herein, all technical and scientific terms used herein have the same meaning as commonly understood by one of ordinary skill in the art to which this invention belongs. Singleton et al., *Dictionary of Microbiology and Molecular Biology,* second edition, John Wiley and Sons, NY (1994), and Hale and Marham, *The Harper Collins Dictionary of Biology,* Harper Perennial, NY (1991) provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

By "compositions", it is meant that probes complementary to *Pseudo-nitzschia* rRNA may be in a pure state or in combination with other probes. In addition, the probes may be in combination with salts or buffers, and may be in a dried state, in an alcohol solution as a precipitate, or in an aqueous solution.

The phrase "and combinations thereof," in the context of *Pseudo-nitzschia* species, refers to compositions of probes designed to detect one or more of the *Pseudo-nitzschia* species stated. The probes may be a mixture of different probes capable of detecting a single species or two or more species, a mixture of different probes wherein the probes are each able to detect one or more species. In the context of oligonucleotide sequences, the phrase "and combinations thereof" refers to a composition of copies of a single probe that may contain as a part of the probe one or more copies of a single oligonucleotide sequence or a mixture of the given sequences, or a mixture of probes that may contain as a part of the probes single or multiple copies of the given oligonucleotide sequences.

The terms "oligonucleotide" or "polynucleotide" probes are meant to include both double stranded and single stranded DNA or RNA. The terms also refer to synthetically or recombinantly derived sequences essentially free of non-nucleic acid contamination.

By "marine sample" is meant a specimen of sea water or of an organism living within the sea. The term also encompasses a digestive tract specimen from an organism not living within, but taking nutrition exclusively from, the sea.

By "segment of nucleic acid" is meant a nucleic acid sequence of 10 to 100 nucleotides or nucleotide analogs in length or concatamers of such sequence.

By "permeabalize" is meant disrupting the cell to allow for intracellular or extracellular hybridization between nucleic acid probes and rRNA. A permeabilized cell may be lysed to allow to extracellular release of rRNA, fixed so as to allow entry of probes into the cell, or both.

By "expose rRNA" is meant to render rRNA accessible to hybridization by a complementary segment of nucleic acid.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides.

The term "subsequence" in the context of a particular nucleic acid or polypeptide sequence refers to a region of the nucleic acid or polypeptide smaller than the particular nucleic acid or polypeptide. "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993). Generally, highly stringent wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ point for a particular probe.

By "*Pseudo-nitzschia* species" is meant at least one species of the genus *Pseudo-nitzschia*.

wherein:

a) X is a sequence of 0 to 100 nucleotides or nucleotide analogs that are non-homologous to conserved or non-conserved regions of *Pseudo-nitzschia* nucleic acid;

b) Y is a sequence of 10 to 100 nucleotides or nucleotide analogs that are capable of hybridizing under hybridizing conditions to hypervariable regions of the ribosomal RNA of *Pseudo-nitzschia* species, such that Y may also comprise subsequences that are capable of hybridizing under hybridizing conditions to one or more species of said *Pseudo-nitzschia* species;

c) Z is a sequence of nucleotides the same as or different from X, such that-nucleotides or nucleotide analogs are non-homologous to conserved or non-conserved regions of nucleic acid of *Pseudo-nitzschia*; and d) n is 1–500, or more and, where n is greater than 1, Y can be the same or different sequences of nucleotides having said hybridization capability. The probe can be free or contained within a vector sequence (e.g., plasmids or Single Stranded DNA).

The probes provided herein detect *Pseudo-nitzschia* of the following species: *P. australis, P. pungens, P. multiseries, P. pseudodelicatissima, P. heimii, P. fraudulenta, P. delicatissima, P. americana.* This invention discloses compositions comprising polynucleotide probes able to hybridize to rRNA of these species. Ribosomal rRNA target regions for said probes are provided in Table 1.

TABLE 1

| Probe designation | Targeted Pseudo-nitzschia species | Probe sequence 5'–3' | SEQ ID NO: | Target sequence 5'–3' | SEQ ID NO: |
|---|---|---|---|---|---|
| Probes for Sandwich hydridization ||||||
| auD1-S | australis | AAATGACTCACTCCACCAGGCGG | 17 | CCGCCUGGUGGAGUGAGUCAUUU | 1 |
| puD1-S | pungens | TGACTCACTTTACCAGGCGG | 18 | CCGCCUGGUAAAGUGAGUCA | 2 |
| muD1-S | multiseries | AAATGACTCACTCTGCCAGG | 19 | CCUGGCAGAGUGAGUCAUUU | 6 |
|  |  |  | 20 |  | 8 |
| muD2-S | multiseries and pseudodelicatissima | AGCCCACAGCGCCCAAGCCA |  | UGGCUUGGGCGCUGUGGGCU |  |
| Pseud-S | all | CTCTTTAACTCTCTTTTCAAAGTTCTT TGCATC | 21 | GAUGCAAAGAACUUUGAAAAGAGAGU UAAAGAG | 16 |
| Probes for whole cell hybridization ||||||
| auD1 | australis | AAATGACTCACTCCACCAGG | 22 | CCUGGUGGAGUGAGUCAUUU | 2 |
| puD1 | pungens | ATGACTCACTTTACCA | 23 | UGGUAAAGUGAGUCAU | 4 |
| puD2 | pungens | AAGTCCACAGCGCCCAGGCC | 24 | GGCCUGGGCGCUGUGAGCUU | 5 |
| muD1 | multiseries | ATGACTCACTCTGCCA | 25 | UGGCAGAGUGAGUCAU | 7 |
| muD2 | multiseries | AAGCCCACAGCGCCCAAGCC | 26 | GGCUUGGGCGCUGUGGGCUU | 9 |
| heD1 | heimii | CCATGACTCATTCTACCAGA | 27 | UCUGGUAGAAUGAGUCAUGG | 10 |
| heD2-1 | heimii | CAAGGGAAATATGAACATA | 28 | UAUGUUCAUAUUUCCCUUG | 11 |
| heD2-2 | heimii | TATCCACAGCGCCCACA | 29 | UGUGGGCGCUGUGGAUA | 12 |
| frD1 | fraudulenta | AAAGACTCATTCTACCAGG | 30 | CCUGGUAGAAUGAGUCUUU | 13 |
| deD1 | delicatissima | AGACTCACTCTACCA | 31 | UGGUAGAGUGAGUCU | 14 |
| amD1 | americana | ATGACTCATTCAGCCA | 32 | UGGCUGAAUGAGUCAU | 15 |

By "open region" is meant a subsequence of nucleic acid having minimal secondary or tertiary interactions with adjacent nucleotides.

By "closed region" is meant a subsequence of nucleic acid with significant secondary or tertiary structure.

Probes

The probes of the present invention are generally of the formula:

[X—Y—Z]$_n$

The nucleic acid sequence of the claimed probes include synthetically derived or recombinant nucleic acid sequences which have sufficient identity with the claimed sequences that they substantially hybridize with regions complementary to the claimed probes. By "substantially", it is meant that under standard hybridization conditions of moderate stringency, percent hybridization can be shown to exceed 50% of the hybridization between perfectly complementary nucleic acid fragments.

The probes of the present invention substantially bind, under selective hybridizing conditions, only to regions of *Pseudo-nitzschia* rRNA having minimal secondary or tertiary interactions with adjacent nucleotides, such regions termed "open regions." By "substantially bind" it is meant that the probes do not comprise significant sequences that bind to regions that are available for hybridization only after heating, that is, regions with significant secondary and tertiary structure (closed regions) . In practical terms, such probes will generally not comprise any more than 10 flanking nucleotides (either 5' or 3') which would bind to closed regions. More specifically, compositions of polynucleotide probes complementary to open regions are claimed that are complementary to either the hypervariable or, alternatively, to the conserved regions of rRNA of *Pseudo-nitzschia* species.

The probes of the present invention may be a compound of RNA or DNA or chimera thereof. In addition, analogs of nucleosides may be substituted for naturally occurring nucleosides. The advantage of analogs would include greater stability, resistance to nuclease activity and ease of signal attachment. The term "probe" is intended to embrace all functionally equivalent species. Equivalent *Pseudo-nitzschia* probes may also consist of the given sequence, concatemers of the sequence, or probes flanked by about 10 or less bases of any degree of complementarity to the native sequences flanking the complementary region of *Pseudo-nitzschia* rRNA.

The probes of the present invention may be chemically synthesized using commercially available methods and equipment. Methods of synthesizing nucleic acids are well known in the art. Deoxynucleotides may be synthesized chemically according to the solid phase phosphoramidite triester method described by Beaucage and Caruthers, *Tetrahedron Letts.* 22(20):1859–1862 (1981), e.g., using an automated synthesizer, e.g., as described in Needham-VanDevanter et al., *Nucleic Acids Res.* 12:6159–6168 (1984).

To obtain large quantities of oligonucleotide probes, one can also clone the desired sequence using traditional cloning methods, such as described in Maniatis, T., et al. *Molecular Cloning: A Laboratory Manual,* Cold Spring Harbor, New York (1982), or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host. The DNA probes can be purified from the host cell by lysis and nucleic acid extraction, treatment with selected restriction enzymes, and further isolation by gel electrophoresis. The use of polymerase chain reaction technology can also be used to obtain large quantities of probe. (See U.S. Pat. No. 4,683,202.)

Sample Collection and Treatment

The present invention is also directed to a method of detecting a *Pseudo-nitzschia* species from a marine sample. These methods comprise the steps of: permeabilizing the cells of the *Psuedo-nitzschia* species to expose the ribosomal RNA; contacting said ribosomal RNA, under hybridizing conditions, with polynucleotide probes capable of selectively hybridizing to a hypervariable or conserved region of the ribosomal RNA of said species; and detecting hybridization complexes as an indication of the presence of the species in the sample.

Marine samples for use in this invention can be obtained by any number of methods well known to the skilled artisan including tow samples of marine waters, tissue samples from marine organisms, or gastric or intestinal contents of organisms taking nutrition from marine organisms. The samples may be subsequently processed, for example, to remove precipitated material, to concentrate or dilute the sample, filtered to exclude organisms of particular size, or cultured to enrich or deplete the population of particular organisms. Conveniently, the sample is dispersed in a buffer protective of, or compatible with, rRNA such as Lugol's iodine (Boney, A.D., *Phytoplankton, Studies in Biology,* no. 52 (1979)).

The sample, or a portion thereof, may be permeabilized for use in a sandwich hybridization assay in a lysis buffer such as disclosed in Van Ness et al., *Nucl. Acids. Res.* 19:5143–5151 (1991), and PCT application WO 93/24659, both incorporated herein by reference. Lysing solutions are well known in the art and are typically composed of a buffered detergent solution having a divalent metal chelator or a buffered chaotrophic salt solution containing a detergent (such as SDS), a reducing agent and a divalent metal chelator (EDTA). Generally, these buffers are between pH 7.0 and 8.0, and contain both chelating agents and surfactants.

Mechanical methods, including French press, nitrogen cavitation, bead beater, ultrasound sonification, may also be employed to permeabalize the cell. Alternatively, samples may be collected and dispersed in a lysing solution that also functions as a hybridization solution, such as 3M guanidinium thiocyanate (GuSCN), 50 mM Tris (pH 7.6), 10 mM EDTA, 0.1% sodium dodecylsulfate (SDS), and 1% mercaptoethanol (Maniatis, et al., *Molecular Cloning: A Laboratory Manual,* Cold Spring Harbor, NY (1982).

Methods for in situ hybridization are also applicable to this invention. In situ hybridization (or whole cell hybridization) refers to the identification of *Pseudo-nitzschia* cells using polynucleotide probes, wherein the intact cell is immobilized and provided as a target. The following two review articles provide an overview of the art of in situ hybridization: Singer et al., *Biotechniques* 4(3) :230–250 (1986), and Haase et al., *Methods in Virology,* Vol. VII, pp. 189–226 (1984), and are incorporated by reference herein.

Hybridization Conditions

Assay test protocols for use in this invention are those of convention in the field of nucleic acid hybridization, and include both single phase, where the target and probe polynucleic acids are both in solution, mixed phase hybridizations, where either the target or probe polynucleotides are fixed to an immobile support including a mixed phased, non-sandwich type assay. Whole cell hybridization may also be employed using methods well known in the art and exemplified herein. The assay test protocols known to the skilled artisan are varied and are not to be considered a limitation of this invention.

Various hybridization solutions may be employed, comprising from about 20 to 60% volume, preferably 30%, of a polar organic solvent. A common hybridization solution employs about 50% v/v formamide, about 0.5 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, 0.01–0.05% ficoll (about 300–500 kilodaltons), 0.01–0.05% polyvinylpyrrolidone (about 250–500 KDa), and 0.01–0.05% serum albumin. Also included in the typical hybridization solution will be unlabeled carrier nucleic acids from about 0.1 to 5 mg/ml, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, or polystyrene sulfonic acid and anionic saccharidic polymers, such as dextran sulfate.

An alternative hybridization solution may be employed comprising about 2 to 4M GuSCN, preferably 3M, about 0.01 to 0.1M Tris (pH range about 6.0 to 8.5), a detergent such as sodium dodecyl sulfate in concentrations of about 0.1 to 5% (w/v), and about 0.01 to 0.1M EDTA. Other additives may also be included such as carrier DNA or RNA, or protein such as bovine serum albumin or gelatin. Stringency of the hybridization solution can be adjusted by the addition of about 0 to 10% formamide, usually 5%.

The particular hybridization technique is not essential to the invention. Hybridization techniques are generally described in *Nucleic Acid Hybridization: A Practical Approach,* Ed. Hames, B. D. and Higgins, S. J., IRL Press (1987); Gall et al., *Proc. Natl. Acad. Sci., U.S.A.,* 63:378–383 (1969), and John et al. *Nature,* 223:582–587 (1969). As improvements are made in hybridization techniques, they can readily be applied.

Regardless of the assay test protocol being used, the *Pseudo-nitzschia* cells are to remain in contact with a hybridization solution for an extended period of time. In single phase assays, the double-stranded duplexes may be separated from single-stranded nucleic acid by $S_1$ nuclease digestion followed by precipitation of duplex molecules, or by selective binding to hydroxyapatite. In mixed phase assays, the support-immobilized nucleic acid is typically introduced into a wash solution having analogous concentrations of sodium chloride, buffers, and detergent, as provided in the hybridization solution. The time period for which the support is maintained in the wash solution may vary from several minutes to three hours or more.

The amount of labeled probe which is present in the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

Either the hybridization or the wash medium can be stringent. Typically, for mixed phase assays, it is the wash solution that most often determines the stringency and facilitates dissociation of mismatched duplexes. After rinsing the support at room temperature with a dilute buffered sodium chloride solution, the support may now be assayed for the presence of duplexes in accordance with the nature of the label.

In a sandwich-type assay a primary component is a solid support. The solid support has adsorbed to it or covalently coupled to it immobilized nucleic acid probe that is unlabeled and complementary to one portion of the rRNA sequence. Probes hybridize to regions of the ribosomal RNA with minimal secondary and tertiary interactions, such as those listed in Table 1. The advantage of such probes is that the hybridization can be carried out without the additional step of heat denaturing the sample nucleic acid.

For the sandwich-type assay, the test sample suspected of containing *Pseudo-nitzschia* is then contacted with the solid support in a hybridization medium. Finally, a second soluble-labeled probe complementary to a different sequence of the rRNA of the pathogenic *Pseudo-nitzschia* is hybridized to the rRNA that has formed a hybridization duplex with the immobilized nucleic acid probe on the solid support. A probe to a hypervariable region and a probe to a conserved region of rRNA of *Pseudo-nitzschia* may each function as either a capture or signal probe. Conveniently, the entire assay takes place at room temperature.

The presence of *Pseudo-nitzschia* species assayed from the marine sample is then determined in accordance with the label being used. It should be noted that in sandwich hybridization the second probe can be added simultaneously with the test sample to the hybridization assay. In addition the second probe can hybridize to either a conserved or to a hypervariable region of the rRNA.

Detection

Where the label is radioactive, the presence of probe can be detected in a scintillation counter. More conveniently, in mixed phase assays, the substrate can be dried and exposed to X-ray film in any number of conventional autoradiographic protocols. Autoradiographic detection is typically employed with $^3H$, $^{125}I$, $^{35}S$, $^{14}C$, or $^{32}P$ labeled probes or the like. The choice of radioactive isotope depends on research preferences due to ease of synthesis, stability and half lives of the selected isotopes.

Where the label is fluorescent, the sample is detected by first irradiating it with light of a particular wavelength. The sample absorbs this light and then emits light of a different wavelength which is picked up by a detector.

Where the label is a hapten or antigen, the sample can be detected by using antibodies. In these systems, a signal is generated by attaching fluorescent or enzyme molecules to the antibodies; in some cases the antibody is labeled with a radioactive probe. (Tijssen, P., *Practice and Theory of Enzyme Immunoassays, Laboratory Techniques in Biochemistry and Molecular Biology,* Burdon, R. H., van Knippenberg, Ph. H., Eds., Elsevier, pp. 9–20 (1985).)

One method of detection is enzymatic detection in conjunction with biotin. Although fluorescence is an alternative label, enzymatic labels, in combination with avidin or streptavidin such as biotinylated peroxidase or alkaline phosphatase, are preferred. Enzyme-conjugated avidin or streptavidin can also be used to directly bind the enzyme to the probe. Preferred enzymes are peroxidase or alkaline phosphatase.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz, et al., *Nuc. Acids Res.* 12:3435–3444 (1984)) and synthetic olignucleotides have been coupled directly with alkaline phosphatase (Jablonski et al., *Nuc. Acids. Res.* 14:6115–6128 (1986). A general reference for various detection methods can be found in Hames, B. D. and Higgins, S. J., *Nucleic Acid Hybridization,* IRL Press, Oxford (1985). References for sandwich assay with DNA probes are Dunn and Hassell, *Cell, Vol.* 12, pp. 23–26 (1977), and Ranki, et al., U.S. Pat. No. 4,486,539.

Kits

The oligonucleotide or polynucleotide acid probes of this invention can be included in a kit which can be used to rapidly determine the presence or absence of *Pseudo-nitzschia* species from a marine sample, in particular, the species disclosed in Table 1 (above). The kit includes all components necessary to assay for the presence of these species. The kit includes a stable preparation of labeled probes to rRNA, hybridization solution in either dry or liquid form for the hybridization of target and probe polynucleotides, as well as a solution for washing and removing undesirable and nonduplexed polynucleotides, and a substrate for detecting the labeled duplex.

A more specific embodiment of this invention embraces a kit that utilizes the concept of the sandwich assay. This kit would include as a first components, vials for containment of a marine sample and buffers for the permeabilization of the sample. A second component would include media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is(are) complementary to a part of the rRNA of the species assayed for. In the case of multiple target analysis more than one capture probe, each specific for its own ribosomal RNA, will be applied to different discrete regions of the dipstick. A fourth component would contain labeled probe that is complementary to a second and different region (conserved or hypervariable) of the same rRNA strand to which the immobilized, unlabeled nucleic acid probe of the third component is hybridized.

The probe components described herein include coordinations of probes in dry form, such as lyophylized nucleic acid or in precipitated form, such as alcohol precipitated nucleic acid or in buffered solutions. The various reagents for the detection of labeled probes and other miscellaneous materials for the kit, such as instructions, positive and negative controls, and containers for conducting, mixing, and reacting the various components, would complete the assay kit. Such kits would include instruction cards and vials containing the various solutions necessary to conduct a nucleic acid hybridization assay. These solutions would include lysing solutions, hybridization solutions, combination lysing and hybridization solutions, and wash solutions. The kits would also include labelled probes. Standard references for comparison of results may also be provided for an easy estimate of the number of *Pseudo-nitzschia* species in a given solution. Depending upon the label used additional components may be needed for the kit, e.g., enzyme labels require substrates.

Probes Complementary to the rRNA of *Pseudo-nitzschia* Species

The degree of complementarity (homology) required for detectable binding of probes of the present invention with the rRNA of *Pseudo-nitzschia* will vary in accordance with the stringency of the hybridization medium and/or wash medium. The degree of complementarity will optimally be 100 percent; however, it should be understood that minor variations between the rRNA and the disclosed probes may still provide for selective hybridization to a particular rRNA without undesired cross-hybridization to other accessible nucleic acids in the sample. Such minor variations may be compensated for by reducing the stringency of the hybridization and/or wash medium as described below. Thus, despite the lack of 100% complementarity under reduced conditions of stringency, functional probes having minor base differences from their rRNA targets are possible. Therefore, under hybridization conditions of reduced stringency, it may be possible to slightly modify the disclosed probes while maintaining an acceptable degree of specificity to detect the desired *Pseudo-nitzschia* species present in the sample.

From the foregoing description it will be clear to those of skill in the art that both whole cell and sandwich hybridization techniques are useful for identifying *P. australis* collected from pure cultures or nature. Moreover, both techniques offer promising means by which one could quantify this species rapidly. Neither protocol is extremely complicated or demanding, and with minimal training all individuals should be able to execute both methods. The choice of one technique over another might depend on the type of data one wishes to obtain (visual cell counts, or indirect estimates based on color change), the speed at which one desires an estimate of the presence and abundance of *P. australis,* the number of samples to analyze, and equipment available to the researcher. Whole cell and sandwich hybridization each offer their own advantages and disadvantages.

Whole cell hybridization assays take approximately 3 hours to complete (from live sample to labeled cells). Of this time, as much as 1.5 hours are required of the person performing the assay; this does not include labor required to view filters and enumerate target species. Regarding the latter, we find it takes 10–30 min to examine a filter and count labeled cells; the actual time spent depends on the density of material collected, the number of labeled cells present, and the magnification used when viewing the filter. Equipment required to execute the whole cell hybridization protocol as described here includes a filtration manifold, water bath or dry incubator, micro pipette, and an epifluorescence microscope. The lower limit of detection (LLD) of this method is not known, but is related to the volume of water filtered and the ratio of target species to non-target material (cells and organic matter). Given our current protocol and equipment, it is possible to detect as few as 50 cells $1^{-1}$ in samples that were not pre-concentrated (i.e., whole water samples) prior to loading the filter stack.

Compared to the whole cell method, sandwich hybridization is several fold faster and far less taxing on the individual executing the protocol. Equipment used to apply this method includes a standard filtration manifold, heating block, micro pipette, and the robotic processor and reflectance scanner. The latter costs several thousand dollars less than an average epifluorescence microscope and is available commercially. It is possible to apply this method outside of a laboratory, but one must have the means to control reaction temperature (the same is true for whole cell hybridization). Using current technology, the LLD for sandwich hybridization is roughly $2.5–5 \times 10^2$ *P. australis* cells 0.5 ml$^{-1}$ of lysate. The lowest number estimated thus far is 95 cells 0.5 ml$^{-1}$ lysate, a value that corresponded to 95 *P. australis* in 1 ml of a highly concentrated net tow sample that contained many species of plankton as well as particulate organic matter (quantitative whole cell hybridization of the same material gave an estimate of 80 P. australis ml$^{-1}$). For whole water samples, it is possible to detect as few as several hundred to 10$^3$ cells extending from position 198–220 in the amplified fragment (Scholin et al., *Natural Toxins* 2:152–165 (1994)). To date, no LSU sequence data are available for *P. pseudodelicatissima*.

TABLE 2

| | | Whole Cell Hybridization | | | Sandwich Hydridization | | |
|---|---|---|---|---|---|---|---|
| | | | | | | | Number of cells added to |
| Species designation[a] | Predicted LSU rRNA sequence (5'–3') | + control[b] | – control[b] | aus-D1[b] | – control[b] | aus-specific[b] | – control and aus-specific beads[c] |
| *P. australis* -- SEQ ID NO.: 1 | CCGCCUGGUGGAGUGAGUCAUUU | ++ | -- | ++ | -- | ++ | 439.600 |
| *P. multiseries* SEQ ID NO.: 33 | ........ CA ............. | ++ | -- | -- | -- | -- | 969.800 |
| *P. pungens* SEQ ID NO.: 34 | .......... AA ............ | ++ | -- | -- | -- | -- | 517.100 |
| *P. delicatissima* SEQ ID NO.: 35 | .......... A .......... - ... | ++ | -- | -- | -- | -- | 4.819.600 |
| *P. americana* SEQ ID NO.: 36 | ........ CU .. A .......... | ++ | -- | -- | -- | -- | 11.914.800 |
| *P. heimii* SEQ ID NO.: 37 | .......... A .. A ....... - ... | ++ | -- | -- | -- | -- | 842.300 |
| *P. fraudulenta* SEQ ID NO.: 38 | ... U ..... A .. A ........ GG | ++ | -- | -- | -- | -- | 1.218.000 |
| *P. pseudodelicatissima* | not determined | ++ | -- | -- | -- | -- | 1.366.700 |

[a]as determined by criteria and methods outlined in Hasle, G. R., Skr. Norske Videnskaps-Akademi i Oslo, Mat.-Naturv. Klasse Ny Series 18:1–45 (1965) & Scholin et al. 1994b
[b]++ = bright stain; -- = no stain; see FIG. 3.
[c]estimated by: {[(number of cells/ml culture) × (ml harvested)] (final volume of lysate)} × fraction of lysate added to each well of a microtiter plate number lysed cells added per negative control and aus-specific bead treatments.

1$^{-1}$ using the current sandwich hybridization assay and instrumentation described above.

As with the whole cell method, the LLD may vary depending on the composition of the sample and the volume of water filtered. Although we presently view sandwich hybridization as a less sensitive diagnostic tool than whole cell hybridization, it is nonetheless more than adequate to provide "early warning" of potentially toxic blooms of *P. australis* where one might become alarmed only if cells reach a density of greater than 10$^4$ cells 1$^{-1}$ (Anonymous, *Abstracts, Seventh International Conference on Toxic Marine Phytoplankton,* Sensai, Japan (1995)).

Although the present invention has been described in some detail by way of illustration and example for purposes of clarity of understanding, it will be obvious that certain changes and modifications may be practiced within the scope of the appended claims.

EXAMPLE 1

Example 1 describes a whole cell in situ hybridization assay for *Pseudo-nitzschia australis*.

Culture conditions for *P. australis, P. pungens, P. multiseries, P. americana, P. delicatissima, P. pseudodelicatissima, P. heimii* and *P. fraudulenta* as well as methods for sequencing LSU (large subunit) rDNA are given by Scholin et al., *Natural Toxins* 2:152–165 (1994). Culture light levels were held at a photon flux of 40 mmol m$^{-2}$ shu -1. The sequence of a fragment of LSU rRNA from *P. australis* is shown in Table 2, and is compared to corresponding sequences from other *Pseudo-nitzschia* taxa. Identical nucleotides are indicated by a period and alignment gaps are indicated by a dash. These sequences were deduced from analysis of PCR-amplified LSU (large subunit) rDNA, All solutions were prepared using reagents certified RNase/DNase-free (Sigma). The *P. australis*-specific oligonucleotide for whole cell hybridization (the 'aus-D1 probe,' or 'aus-D1') consists of the sequence 5'AAATGACT-CACTCCACCAGG3' (SEQ ID NO:22). The uniqueness of this probe was checked against all sequences available in the rRNA data base (the ribosomal database (RDP) project at the University of Illinois at Urbana; version 4.0; Maidak et al., *Nucleic Acids Research* 22:3485–3487 (1994)), revealing no potential cross reactions with 3 or fewer base pair mismatches. Aus-D1 was synthesized commercially and coupled to fluorescein at the 5' end (Oligos Etc., Eugene, OR). The purified probe was resuspended at a concentration of 250 ng ml$^{-1}$ in distilled water, aliquoted to multiple 0.6 ml tubes, then vacuum desiccated (Speed Vac) and stored at –40° C. A working stock of aus-D1 was prepared by resuspending a dried aliquot in TE buffer (10 mM Tris HCl, 1 mM EDTA, pH 7.4) at a final concentration of 100 ng ml$^{-1}$. Universal 'positive control' [5'G(A/T)ATTACCGCGGC(G/T)GCTG3' (SEQ ID NO:39); small-subunit (SSU) rRNA-targeted ('519 reverse'; Field et al., *Science,* Washington, D.C. 239:748–753 (1988); Embley et al., *Journal of General Microbiology* 138:1479–1487 (1992))] as well as 'negative control' [5'AGTGCAACACTCCCACCA3' (SEQ ID NO:40); LSU rRNA-targeted to North American ribotype *Alexandrium tamarense* (Lebour) Balech; Scholin et al., *Journal of Phycology* 30:999–1011 (1994)] probes were prepared as above. The positive control probe should hybridize with rRNA sequences common to all known small sub-unit (SSU) rRNA molecules, whereas the negative control probe was designed for a LSU rRNA sequence potentially specific for one strain of *A. tamarense*. The latter is directed against a sequence of LSU rRNA that is in a position of the molecule similar to that targeted by aus-D1.

An ethanol/saline fixative was prepared by adding 2 ml dH$_2$O, 3 ml 25×SET buffer (3.75 M NaCl, 25 mM EDTA, 0.5 M Tris HCl, pH 7.8) and 25 ml of 95% ethanol (Gold Shield Chemical Co., Hayward, Calif.) in a 50 ml polypropylene, conical bottom, disposable centrifuge tube. Approximately 10–20 ml of exponentially growing cells were added to this freshly prepared solution and left overnight to 3 days at 4° C. Cells were collected by centrifugation (3–3.500×g) in a swinging-bucket rotor at room temperature for 5–10 min. The cell pellet, along with some of the supernatant, was transferred to a 1.5 ml micro centrifuge tube. Cells were pelleted as above, except that centrifugation was limited to 3 min. As much supernatant as possible was removed, and cells were rinsed briefly in 500–750 ml freshly prepared hybridization buffer [5×SET (1/5 dilution of above), 1% (v/v) Nonidet P-40 (Sigma), 12.5 mg/ml polyadenlyic acid (poly A; Sigma)]. Cells were pelleted as before, then resuspended in 150 ml of hybridization buffer. Approximately 47.5 ml of this slurry was aliquoted to 3, 0.6 ml tubes containing 2.5 ml (250 ng) of the positive control, negative control, or aus-D1 fluorescein-labelled probes. Hybridization occurred for 3–4 h at 45° C. in a darkened water bath; during this time cells were resuspended on several occasions by gently tapping the tubes. To terminate the labelling reactions, 100 ml of 0.2×SET (1/125 dilution of above) was added and cells were centrifuged as above. Cell pellets were resuspended in 175 ml pre-warmed (45° C.) 0.2×SET, incubated at 45° C. for no more than 3 min, and pelleted as above. Supernatant was removed, leaving approximately 20 ml behind; 20 ml of SlowFade (Molecular Probes, Eugene, Oreg.) was added and cells mixed thoroughly. Approximately 5–10 ml of this slurry was spotted onto a standard microscope slide, and viewed using a Zeiss Axioskop fitted with fluorescein band-pass filter (excitation 465–495 nm; dichroic 505 nm; emission 515–555 nm) and Olympus 10AD 35 mm camera system. All probe treatments were photographed at a constant exposure setting (32 s) using Kodak ASA 400 Gold Plus print film. Corresponding transmitted light images were also documented for cells hybridized to the negative control and aus-D1 probes. Labelled cells were stable for $\geq 24$ h when stored in the dark at 4° C. This protocol is a modification of that described by DeLong et al., *Science, Washington, D.C.* 243:1360–1363 (1989).

Results of whole cell hybridization experiments are compiled in Table 1. All species tested retained the positive, but not the negative control probe. The positive control treatments demonstrate that fluorescein-labelled oligonucleotides bind universally conserved sequences of SSU rRNA in *Pseudo-nitzschia* preserved with an ethanol-based fixative. Results obtained using the negative control probe show that non-specific retention of a fluorescein-labelled oligonucleotide of similar size and GC content as aus-D1 is negligible. Given this range of responses one can thus judge the efficacy of a novel probe such as aus-D1. As seen in Table 1, the aus-D1 probe clearly labels *P. australis* but not other species examined despite the fact these organisms differ by as few as 2 nucleotides in the targeted region of LSU rRNA.

EXAMPLE 2

Example 2 describes a sandwich hybridization assay for *Pseudo-nitzschia australis.*

The *P. australis*-specific 'capture probe' attached to nylon beads consists of the sequence 5'AAATGACTCACTCCAC-CAGGCGG3' (SEQ ID NO:17) (a longer version of aus-D1). Conjugation of the capture probe to the beads was accomplished as described by Van Ness et al., *Nucl. Acids. Res.* 19:5143–5151 (1991); beads supplied by Hoover Precision Products, Sault Sainte Marie, Mich.). Hereafter, the *P. australis*-specific oligonucleotide/bead conjugate is referred to as the 'aus-specific bead.' The signal probe consists of the sequence 5' CTCTTTAACTCTCTTTTCAAAGT-TCTTTGCATC3' (SEQ ID NO:21), coupled to biotin at its 5' end (Van Ness et al., *Nucl. Acids. Res.* 19:5143–5151 (1991)). The signal probe is targeted towards a LSU rRNA sequence conserved among all *Pseudo-nitzschia* compared to date.

Sandwich hybridizations were conducted in a similar manner as that described by Van Ness et al., *Nucl. Acids. Res.* 35 19:5143–5151 (1991). Approximately 20–50 ml of exponentially growing cells cultured under conditions described in Example 1 were collected by centrifugation as above. The cell pellet, along with some of the supernatant, was transferred to a 1.5 ml micro centrifuge tube and collected as before. After removing as much supernatant as possible, cells were resuspended in 400 µl of lysis solution [50 mM glycine, 10 mM EDTA, 5% (v/v) N-lauryl sarcosine, 0.5% (v/v) ProClin 150 (a preservative from Rohm and Haas, Philadelphia, Pa.), pH 11], and heated to 85° C. for 5 min.; 600 µl of hybridization buffer (100 mM Tris, 17 mM EDTA, 8.35% formamide, 5 M guanidine thiocyanate, pH 7.5) were added, and the sample mixed well. The lysate was transferred to a filter tube (Porex, Fairburn, Ga.), pushed through to remove particulates >1 mm, and filtrate was collected in a fresh 1.5 ml centrifuge tube. Approximately 400 µl of this crude lysate were added to each of 2 wells of a standard 48 well microwell plate. Three aus-specific beads were added to the first well, and 3 'negative control beads' were added to the second. The negative control beads are an oligonucleotide/nylon bead conjugate that does not hybridize with any known rRNA (MicroProbe Corp., Bothell, Wash.). The latter serves as a procedural control to ensure that observed colour development is specific to complete capture probe/target/signal probe sandwiches. The microwell plate was placed on an orbital shaker so that the beads rotated gently within the wells. Primary hybridization reactions were allowed to proceed for 30 min at 23–25° C. Afterwards, the lysate was aspirated away and replaced with 400 µl of secondary hybridization solution (100 mM Tris, 17 mM EDTA, 8.35% formamide, 3 M guanidine thiocyanate, pH 7.5) containing 1 µg ml$^{-1}$ of biotinylated signal probe. Secondary hybridization reactions were carried out as above. Beads were rinsed twice using 1 ml of wash solution [50 mM Tris HCl, 10 mM EDTA, 100 mM NaCl, 1% (v/v) sodium dodecyl sulphate, 1% (v/v) N-lauryl sarcosine, pH 8.0] and agitation as above for 2 min. Afterwards, 400 µl of horseradish peroxidase (HRP)-avidin conjugate was added (MicroProbe Corp.), and incubated for 30 min as before. Beads were then rinsed 4 times as above. HRP substrate (MicroProbe Corp.) was added, and colour development was allowed to proceed for 30 min. Beads were removed from solution, dried on a paper towel, and photographed.

Results of sandwich hybridization trials are compiled in Table 2 (above). The aus-specific beads clearly recognize LSU rRNA sequences indicative of *P. australis,* but do not capture molecules from other closely related congeners. As in the whole cell assay, this discrimination was possible even though the *P. australis*-specific LSU rRNA target sequence differs from those of other *Pseudo-nitzschia* representatives by as few as 2 nucleotides, and when the aus-specific beads were thoroughly saturated with LSU rRNA from non-target species.

In conclusion, both whole cell and sandwich hybridization techniques are useful for identifying cultured *P. aus-*

*tralis* using LSU rRNA-targeted oligonucleotide probes. On both accounts it was possible to devise relatively simple protocols to discriminate that organism from its cultured, co-occurring congeners. With minimal training, non-molecular biologists should be able to execute both methods.

EXAMPLE 3

Example 3 describes the identification of cultured *Pseudo-nitzschia* using species-specific large subunit rRNA-targeted fluorescent probes.

Culturing and Species Identifications

Cultures used in this study are listed in Table 1; all are clonal isolates established by pipeting single cells, or chains of cells, sequentially through droplets of sterile sea water. Cultures were maintained in sterile-filtered f/2-enriched sea water (Guillard, R. R. L., *Culture of Marine Invertebrate Animals* (Eds. Smith, et al.), pp. 29–60, Plenum Publishing Corp., NY (1975); f/2 nutrients as supplied by Fritz Chemical Co., Dallas, Tex.) at a salinity of 33% and a temperature of 13° C. Light was provided by cool white fluorescent tubes at a photon flux of 40 $\mu$mol•m$^{-2}$•sec$^{-1}$ on a 10:14 h light-:dark cycle.

Aliquots of cultures were treated to remove organic material by oxidation with $KMnO_4$ and HCl (Hasle, G. R. and Fryxell, G. A., *American Microscopy Society Transactions* 89:460–474 (1970); Simonsen, R., *Deutsche Forschungsgemeinschaft, Reihe D* 19:1–107 (1974)). Samples were then either dried onto glass cover slips or filtered onto polycarbonate membranes (Poretics Corp., Livermore, Calif.). These were affixed to aluminum stubs with silver paint, sputter coated with gold-palladium, and viewed using either a JEOL T330A or ISI WB6 scanning electron microscope. Identification of species followed the description of Hasle (Hasle, G. R., *Skr. Norske Videnskaps-Akademi i Oslo, Mat.-Naturv. Klasse Ny Series* 16:1–46 (1964); Hasle, G. R., *Skr. Norske Videnskaps-Akademi i Oslo, Mat.-Naturv. Klasse Ny Series* 18:1–45 (1965); Hasle, G. R., *Nova Hedwigia, Beih.* 106:315–21 (1993); Hasle, G. R., *J. Phycol.* 30:1036–9 (1994); Hasle, et al., *J. Phycol.* 31:42835 (1995)).

GenBank accession numbers of LSU rDNA sequences are as follows: *P. americana* (U41390), *P. australis*.1 (U40850), *P. australis*.2 (U41393), *P. delicatissima* (U41391), *P. pungens*.1 (U41262), *P. pungens*.2 (U41392), and *P. multiseries* (U41389). At this time, sequences from *P. fraudulenta* and *P. heimii* are only a fraction of the length as those for the above species. For additional details on sequence analyses see Scholin et al., *Natural Toxins* 2:152–165 (1994).

Whole Cell Hybridization

A compilation of probes used in this study, their sequences, and associated hybridization conditions are presented in Table 3. We included positive and negative control treatments to define a range of labeling intensities possible for any given culture. The positive control probe is targeted toward a universally conserved sequence of the SSU rRNA (519r, Field et al., *Science, Washington, D.C.* 239:748–753 (1988); Embley et al., *Journal of General Microbiology* 138:1479–1487 (1992)). The negative control, targeted toward LSU rRNA, is specific for North American strains of *Alexandrium tamarense* (Lebour) Balech (Scholin et al., *Journal of Phycology* 30:999–1011 (1994)).

Oligonucleotides were synthesized with fluorescein attached to their 5' end (Oligos Etc., Eugene, Oreg.). Probes were resuspended at a concentration of 250 ng•mL$^{-1}$ in distilled water, aliquoted to multiple 0.6 mL tubes, then vacuum desiccated and stored at −40° C. Working stocks were prepared by resuspending a dried aliquot in TE buffer (10 mM Tris HCl, 1 mM EDTA, pH 7.4) at a final concentration of 100 ng•mL$^{-1}$.

For each probe, hybridization was carried out at approximately 8°–22° C. below a calculated probe/target melting temperature (Tm), while wash conditions were set at approximately 2–5° C. above the calculated Tm (Table 3). We have found empirically that these conditions are suitable for determining whether or not a novel probe binds its intended (*Pseudo-nitzschia*) target specifically. However, such conditions are not necessarily "optimal" but instead serve as is a reference point from which to gauge the relative utility of a novel probe.

TABLE 3

Sequences of probes, LSU rRNA target location, and associated hybridization and wash conditions.

| Probe | Sequence (5'–3') | SEQ ID NO: | LSU rRNA target location | Hybridization conditions T° C. | Hybridization conditions SETf | Wash conditions T° C. | Wash conditions SET$^f$ |
|---|---|---|---|---|---|---|---|
| auD1 | AAATGACTCACTCCACCAGG | 22 | 220–201 | 45 | 5x | 45 | 0.2x |
| auD1a | ATGACTCACTCCACCA | 41 | 218–203 | 45 | 5x | 45 | 0.5x |
| puD1 | ATGACTCACTTTACCA | 23 | 218–203 | 45 | 7x | 45 | 1.0x |
| puD2 | AAGTCCACAGCGCCCAGGCC | 24 | 449–430 | 55 | 5x | 55 | 0.2x |
| puD2a | TCCACAGCGCCCAGG | 42 | 446–431 | 55 | 5x | 55 | 1.0x |
| muD1 | ATGACTCACTCTGCCA | 25 | 218–203 | 45 | 5x | 45 | 0.5x |
| muD2 | AAGCCCACAGCGCCCAAGCC | 26 | 449–430 | 55 | 5x | 55 | 0.2x |
| muD2a | CCCACACGCCCAAG | 43 | 446–431 | 55 | 5x | 55 | 1.0x |
| heD1 | CCATGACTCATTCTACCAGA | 27 | 220–201 | 45 | 5x | 45 | 0.2x |
| heD2-1 | CAAGGGAAATATGAACATA | 28 | 421–403 | 45 | 5x | 45 | 0.5x |
| heD2-2 | TATCCACAGCGCCCACA | 29 | 448–431 | 45 | 5x | 45 | 0.2x |
| frD1 | AAAGACTCATTCTACCAGG | 30 | 220–201 | 45 | 5x | 45 | 0.3x |
| deD1 | AGACTCACTCTACCA | 31 | 218–203 | 45 | 5x | 45 | 1.0x |
| amD1 | ATGACTCATTCAGCCA | 32 | 218–203 | 45 | 5x | 45 | 0.7x |
| amD3 | ATATCCAACCACTGTTA | 44 | 647–631 | 45 | 5x | 45 | 0.8x |
| posa | GWATTACCGCGGCKGCTG | 39 | — | 45 | 5x | 45 | 0.2x |

TABLE 3-continued

Sequences of probes, LSU rRNA target location, and associated hybridization and wash conditions.

| | | | LSU rRNA target | Hybridization conditions | | Wash conditions | |
|---|---|---|---|---|---|---|---|
| Probe | Sequence (5'–3') | SEQ ID NO: | location | T° C. | SET[f] | T° C. | SET[f] |
| negb | AGTGCAACACTCCCACCA | 40 | — | 45 | 5x | 45 | 0.2x |
| eubc | GCTGCCTCCCGTAGGAGT | 45 | — | 55 | 5x | 55 | 0.5x | apos = positive control, SSU-targeted universally conserved sequence (519r; Field et al., Science, Washington, D.C. 239: 748–753 (1988); Embley et al., Journal of General Microbiology 138: 1479–1487 (1992)).
bneg = negative control, LSU-targeted, *Alexandrium tamarense* - specific (Scholin et al., Phycologia (1996) (in press)).
ceub = eub338, *eubacteria* specific (Amann et al., Applied and Environmental Microbiology 56: 1919–1925 (1990)).
drRNA complement
ealigned position
f25x SET = 3.75M NaCl, 25 mM EDTA, 0.5M Tris, pH 7.8.

A saline/ethanol fixative was prepared by adding 2 mL dH$_2$O, 3 mL 25×SET buffer (3.75 M NaCl, 25 mM EDTA, 0.5 M Tris HCl, pH 7.8) and 25 mL of 95% ethanol (Gold Shield Chemical Co., Hayward, Calif.) to a 50 mL polypropylene, conical bottom, disposable centrifuge tube. Approximately 10–20 mL of exponentially growing cells were added to this freshly prepared solution and left at room temperature over night. Cells were collected by centrifugation (3–3,500×g) in a swinging-bucket rotor at room temperature for 10 min. The cell pellet, along with some of the supernatant, was transferred to a 1.5 mL micro centrifuge tube. Cells were pelleted as above, except that centrifugation was limited to 3 min. As much supernatant as possible was removed, and cells were rinsed briefly in 500–750 μL freshly prepared hybridization buffer [5×–7×SET (see Table 3), 0.1% (v/v) Nonidet P-40, 25 mg mL$^{-1}$ polyadenylic acid (poly A)]. Cells were pelleted as before, then resuspended in 150 μL of hybridization buffer. Approximately 47.5 μL of this slurry was aliquoted to each of 3, 0.6 mL tubes containing 2.5 μL (250 ng) of either the positive control, negative control, or one of the species-specific probes. Hybridization occurred for 3 h at 45–55° C. in a darkened water bath; cells were resuspended on several occasions by gently tapping the tubes. To terminate the labeling reactions, 100 μL of wash solution were added (0.2–1×SET), and cells were centrifuged as above. Cell pellets were resuspended in 175 μL pre-warmed wash SET, incubated at 45–55° C. for no more than 3 min, then pelleted as before. Supernatant was removed, leaving approximately 20 μL behind; 20 μL of SlowFade Light (Molecular Probes, Eugene, Oreg.) were added and mixed thoroughly. Approximately 5–10 μL of this slurry were spotted onto a standard microscope slide and viewed using a Zeiss Axioskop fitted with fluorescein bandpass filter set (excitation 465–495 nm; emission 515–555 nm) and 50 watt light source. Black and white photos were taken with an Olympus 10AD 35 mm camera system and Kodak Tmax 400 ASA film. Labeled cells were stable for ≧24 h when stored in the dark at 4° C. This protocol is a modification of that described by Scholin et al., *Phycologia* (1996) (in press).

Cultures of the eight Pseudo-ni tzschia species noted above were hybridized with all oligonucleotides listed in Table 3 using indicated hybridization and wash conditions. Cells labeled with an intensity similar to that of positive controls were scored "++" (excellent). Cells labeled with an intensity less than the positive controls, but greater than the negative controls, were scored as "+–" (fair to poor). Those cells not labeled, similar to the negative control, were scored as "– –" (no reaction). Of the fifteen putative species-specific probes evaluated, seven labeled their intended targets specifically with an intensity similar to that of the positive control, three were species-specific with an intensity less than that of the positive control, four cross-reacted with non-target species, and one did not react with any culture examined (Table 4).

TABLE 4

Summary of whole cell hybridization trials. For representative examples of staining intensities see FIG. 2.

| | Probe | | | | | | | |
|---|---|---|---|---|---|---|---|---|
| Species | pos | neg | eub | auD1 | auD1a | puD1a | puD2 | puD2a | muD1 |
| P. australis | + + | – – | + + | + + | + + | – – | – – | – – | – – |
| P. pungens | + + | – – | + + | – – | – – | + + | + – | – – | – – |
| P. multiseries | + + | – – | + + | – – | – – | – – | – – | – – | + + |
| P. heimii | + + | – – | + + | – – | – – | – – | – – | – – | – – |
| p. fraudulenta | + + | – – | + + | – – | – – | – – | – – | – – | – – |
| P. pseudodelicatissima | + + | – – | + + | – – | – – | – – | – – | – – | – – |
| P. delicatissima | + + | – – | + – | – – | – – | – – | – – | – – | – – |
| P. americana | + + | – – | + + | – – | – – | – – | – – | – – | – – |

| | Probe | | | | | | | |
|---|---|---|---|---|---|---|---|---|
| Species | muD2 | muD2a | heD1 | heD2-1 | heD2-2 | frD1 | deD1 | amD1 | amD3 |
| P. australis | – – | – – | – – | – – | – – | – – | – – | – – | – – |
| P. pungens | – – | – – | – – | – – | – – | – – | – – | – – | – – |

TABLE 4-continued

Summary of whole cell hybridization trials. For representative examples of staining intensities see FIG. 2.

| | | | | | | | | | |
|---|---|---|---|---|---|---|---|---|---|
| P. multiseries | + + | + - | - - | - - | - - | - - | - - | - - | |
| P. heimii | - - | - - | + - | + - | + + | + - | - - | - - | - - |
| p. fraudulenta | - - | - - | - - | - - | - - | + + | - - | - - | + - |
| P. pseudodelicatissima | + + | + - | - - | - - | - - | - - | - - | - - | |
| P. delicatissima | - - | - - | - - | - - | - - | + - | + + | - - | + - |
| P. americana | - - | - - | - - | - - | - - | - - | - - | + + | - - |

[a]reactivity of this probe can vary between ++ and +- depending on clone tested.

The positive control probe repeatedly gave a bright and uniform label intensity for all species examined. In contrast, cells did not retain the negative control probe and appeared uniformly dark. The eubacteria-specific probe (eub338, SSU rRNA target; Amann et al., *Applied and Environmental Microbiology* 56:1919–1925 (1990)) labeled chloroplasts of all Pseudo-nitzschia isolates examined, scoring ++ for the majority. The probes auD1 and auD1a (same target site, *P. australis*-specific), puD1 (*P. pungens*-specific), muD1 (*P. multiseries*-specific), heD2-2 (*P. heimii*-specific), deD1 (*P. delicatissima*-specific) and amD1 (*P. americana*-specific) all scored an excellent species-specific response (++). Those probes that labeled their intended target specifically, but only with fair to poor intensity (+-) were puD2 (*P. pungens*-specific) and heD1 (*P. heimii*-specific). Probes that cross-reacted with non-target species were muD2 [++ for *P. multiseries* (target) and *P. pseudodelicatissima* (non-target)], muD2a [+- for *P. multiseries* (target) and *P. pseudodelicatissima* (non-target)], frD1 [++ for *P. fraudulenta* (target), +- for *P. heimii* and *P. pseudodelicatissima* (non-targets)] and amD3 [-- for *P. americana* (target), +- for *P. delicatissima* and *P. fraudulenta* (non-targets)]. The probe puD2a (intended for *P. pungens*) did not react with any species tested.

Eight new cultures of unidentified *Pseudo-nitzschia* were examined using standard light microscopy. Based on cell length and width, we tentatively assigned species designations as either *P. australis*, *P. pungens*, or *P. multiseries*. Each culture was then tested against the probes auD1, puD1 and muD1. Results indicated that two cultures were *P. australis*, two were *P. multiseries*, and three were *P. pungens*. These designations were confirmed using SEM (scanning electron microscopy) to visualize species-specific morphological features. Species identifications were based on criteria established by Hasle (Hasle, G. R., *Skr. Norske Videnskaps-Akademi i Oslo, Mat.-Naturv. Klasse Ny Series* 16:1–46 (1964); Hasle, G. R., *Skr. Norske Videnskaps-Akademi i Oslo, Mat.- Naturv. Klasse Ny Series* 18:1–45 (1965); Hasle, G. R., *Nova Hedwigia, Beih.* 106:315–21 (1993); Hasle, G. R.,*J. Phycol.* 30:1036–9 (1994); Hasle, et al., *J. Phycol.* 31:428–535 (1995)). For *P. australis* these characteristics include a length in the range of 75–144 μm, a width of 6.5–8.0 μm, absence of a central nodule, 12–18 fibulae per 10 μm, 12–18 transapical costae per 10 μm, 2 rows of poroids, and 4–5 poroids per 1.0 μm. The criteria for *P. pungens* are 74–142 μm long by 3–4.5 μm wide, lack of a central nodule, have 9–15 fibulae and transapical costae per 10 μm, 1–2 rows of poroids, and 3–4 poroids per 1.0 μm. Similarly, *P. multiseries* are 68–140 μm by 4–5 μm, lack a central nodule, have 10–13 fibulae and transapical costae per 10 μm, 3–4 rows of poroids, and 4–6 poroids per 1.0 μm. One culture was not labeled with any of the probes tested. In is this case, SEM analysis revealed that it was *P. pseudodelicatissima*, given that it has a central nodule and is within the range of 59 –140 μm long by 1.5–2.5 μm wide, 16–26 fibulae per 10 μm, 30–46 transapical costae per 10 μm, 1 row of poroids, and 4–6 poroids per 1.0 μm. Subsequently, we found that this isolate was labeled with the probe muD2 as expected (Table 4).

We could not predict how probes would react solely on the basis of sequence alignments. Modifying a probe sequence slightly to bind "left" or "right" of the target sequence "center" in some cases did, and in other cases did not, affect its reactivity. Labeling intensities observed for the probes puD2 and muD2 were diminished drastically when each was truncated to give puD2a and muD2a, respectively (Table 4), even though hybridization and wash conditions were such that the probes should have bound their targets. In sharp contrast, truncating the probe auD1 to auD1a had no effect on the intensity with which it labeled its target (Tables 3,4). Similarly, probes that were targeted to different regions of the LSU rRNA, but that were nevertheless directed against the same species, also showed variation in label intensity. For example, of the three probes designed for *P. heimii* only one yielded a response equivalent to the positive controls (Table 4).

Regions of LSU rRNA that served as the "best" targets for specific probes are not the same among all species examined. Instead, the most useful target sites differed despite the fact that the organisms' LSU rRNA sequences are very closely related. In all cases, we presume that the relative strength with which a probe labels a cell is due in part to the accessibility of the target sequence in the context of the 3-dimensional structure of the ribosome; other investigators have drawn similar conclusions (e.g., Vaheri et al. (eds.), *Rapid Methods and Automation in Microbiology and Immunology,* Springer-Verlag, NY (1991)).

We do not yet have species-specific probes for *P. fraudulenta* and *P. pseudodelicatissima*. However, it is possible to identify these organisms using a series of probes with overlapping specificity. For example, the probe frD1 labels *P. fraudulenta* (intended target) well but also cross-reacts to a lesser extent with the non-target species *P. delicatissima* and *P. heimii*. By applying probes that are specific for the latter two (e.g. deD1 and heD2-2), one could assess whether or not cells labeled with frD1 do in fact harbor a signature sequence indicative of *P. fraudulenta*. In addition, one could use gross size and shape characteristics to distinguish *P. fraudulenta* from *P. delicatissima*. Similarly, it should be possible to identify *P. pseudodelicatissima* even though we do not yet know its LSU rRNA sequence. To do this, one could apply the probes muD2 and muD1. The former labels both *P. multiseries* and *P. pseudodelicatissima* equally well, whereas the latter labels *P. multiseries* only (Table 4).

As a first step to determine if probes could recognize novel clones and speed species identifications, we applied several to newly isolated cultures that had not yet been identified using SEM. Preliminary examination of live cultures using light microscopy provided the means to narrow the range of possible species designations on the basis of cell length and width. Given this, we predicted that each clone would hybridize to one of three species-specific probes (auD1, muD1 or puD1). We then tested our prediction empirically. Results of these trials allowed us to assign tentative species designations to seven of the eight clones screened. To verify these assignments, we examined all clones using SEM and identified each using morphological criteria. For seven cultures, identifications based on whole cell hybridization agreed with species designations as defined by morphological features. Thus, the probes recognized their intended targets specifically. The isolate that did not react with auD1, puD1 nor muD1 was revealed by SEM as *P. pseudodelicatissima*. Subsequent analyses showed that this isolate was, however, labeled by muD2, a result that agrees with earlier observations (Table 4). These limited trials suggest that LSU rRNA-targeted probes are useful tools for identifying a variety of cultured *Pseudo-nitzschia* species.

In sum, whole cell hybridization is a useful technique for discriminating between *Pseudo-nitzschia* species. As the number of probes applied to a given sample increases, the greater the confidence one has of the species designation of an organism. By applying a suite of eight probes described here (auD1, puD1, muD1, muD2, heD2-2, frD1, deD1 and amD1) one can discriminate among cultured isolates of *P. australis, P. pungens, P. multiseries, P. heimii, P. fraudulenta, P. delicatissima, P. pseudodelicatissima* and *P. americana* with relative ease.

EXAMPLE 4

Example 4 describes the detection and quantification of *Pseudo-nitzschia australis* in cultured and natural populations using LSU rRNA-targeted probes.

Culturing and Estimates of Cell Density

Unialgal cultures of *P. australis* were isolated, identified and maintained as described previously (Scholin et al., *Natural Toxins* 2:152–165 (1994)). Clones used in this investigation were au 21 and au 22, both of which are held at the Monterey Bay Aquarium Research Institute and the University of California at Santa Cruz. Cell densities were estimated by preserving an aliquot in Lugol's iodine solution (a solution consisting of 10 g of iodine, 20 g of potassium iodine in 200 ml distilled water, with 20 mL of glacial acetic acid added 2–3 days before use), and enumerating the number of cells in 5 ml using light microscopy. The average value s obtained from 3 independent samples was used to calculate cells $ml^{-1}$.

Net tow samples were collected from Monterey Harbor, Calif., using a net with a mesh size of 35 mm. Samples were returned to the lab immediately and placed in a 15° C. incubator. To identify and enumerate the diversity of species present in natural samples, an aliquot was preserved with Lugol's iodine, samples were diluted as necessary, settled in counting chambers, and counted using standard procedures (Guillard, R. R. L., *Handbook of Phycological Methods—Culture Methods and Growth Measurements* (Ed. Stein), pp. 289–311, Cambridge University Press, Cambridge, England (1973)).

Whole Cell Hybridization

A custom filtration manifold was prepared by heat-welding standard 15 ml conical bottom polypropylene centrifuge tubes to 13 mm Swinnex in-line filter housings (Millipore). Filter stacks were attached via a Luer slip fitting to a one-way stopcock (Cole Parmer) which is threaded into ⅜ inch diameter PVC pipe. Vacuum is applied to the manifold by a hand-actuated or electric pump. The entire manifold can be immersed in a water bath or dry incubator to control its temperature.

The sequence of the *P. australis*-specific LSU rRNA-targeted probe ("aus D1") and protocol for its use are given in Example 1. Modifications to that procedure are as follows. Cultured cells or net tow sample were added to the ethanol-based preservative at a ratio of 1 part sample to 5–7 parts fixative. Samples were allowed to stand at room temperature for at least 1 h but no longer than several days. An aliquot of this (0.2–3 ml) was added to the filter stack, and cells in that sample were collected by gentle vacuum filtration onto 13 mm Isopore membranes (1.2–3.0 μm pore size; Millipore). Two to three ml of hybridization solution were added and allowed to stand for several minutes at room temperature. Cells were collected again by vacuum filtration, and 0.5 ml of hybridization buffer containing 5 mg of fluorescein-labeled aus D1 probe were added. Filter stacks were capped and the entire filtration manifold was immersed in a 45° C. water bath for 1 h. The manifold was removed from the bath and cells collected as before. Two ml of hybridization buffer were added, cells were collected immediately, then 2 ml of wash solution were added. The manifold was returned to the 45° C. bath for several minutes, then removed and cells were collected onto the filters. Filters were retrieved while maintaining a slight vacuum, and placed sample-side up on a standard microscope slide. Approximately 20 ml of SlowFade Light (Molecular Probes) was added to the center of the filter, then mounted with a cover slip. Samples were viewed and photographed as described previously. Slides were stored at 4° C. in the dark, where labeled cells were stable for several days.

To estimate the abundance of P. australis cells in the original sample, the entire surface of the filter was viewed and cells were counted, then the following formula was applied: cells $ml^{-1}$ of sample @ (# counted on the filter volume of fixed sample added to the filter stack)×[(total volume of fixative+sample) volume of sample added to fixative]. The first term gives cells $ml^{-1}$ fixed sample, while the second term corrects for sample dilution after fixation. It is also possible to collect cells from live samples and add several ml of fixative to this material. After this stands for 1 h or longer at room temperature, one can proceed as above. The latter modification is useful for processing whole water samples (i.e., those that are not pre-concentrated as is a net tow).

Sandwich Hybridization

The protocol for microtiter plate-based sandwich hybridization assays and a description of necessary reagents are detailed in Example 2. Dilution series of cultured *P. australis* were prepared by adding known numbers of cells (estimated by counts of Lugol's preserved material) to 5 ml of filtered sea water or concentrated net tow. Samples were collected onto 25 mm hydrophilic Durapore membranes (0.65 μm pore size; Millipore) using standard vacuum filtration. Filters were transferred to a filter tube (Porex, Fairburn, Ga.; gift of MicroProbe Corp.) that contained 400 μl of lysis solution, vortexed gently, then heated to 85° C. for 5 min. Afterwards, 600 μl of hybridization buffer were added, the tube was capped with a filter tip and mixed by inversion. The sample was pushed through the filter tip into a clean tube to remove particulates>1 mm. For each sample, 0.5 ml of this crude lysate were added to one well of a standard 24 well microtiter plate, and three "aus-specific beads" were added (nylon beads covalently attached to the *P. australis*-specific capture probe). Hybridization, wash and color development steps followed the procedure noted above. Beads were then dried on a paper towel and photographed.

In the semi-automated assay, solutions required for hybridization, wash and color development steps of the protocol were packaged into "reagent cassettes," and the aus-specific beads were mounted on plastic analytical cards (PACs). The reagent cassettes and PACS were applied using a robotic processor (MicroProbe Corp., Diagnostics Division; see Briselden, et al., *Journal of Clinical Microbiology* 32:148–152 (1994)). The processor was programmed to complete the sandwich hybridization procedure in 32 min. After processing, PACs were allowed to dry for 10 min and color development on the aus-specific bead was quantified using a reflectance scanner (MicroProbe Corp.). Tests of the sandwich hybridization assay as described above were repeated using this instrumentation with the following modifications: duplicate samples were prepared for each point on the standard curves; filters were added to 1 ml of lysis solution; after heating, 1.5 ml of hybridization buffer were added; and, 0.5 ml of filtered lysate from each sample were added to each of 3 reagent cassettes. Target points on the standard curve were thus represented by 2 independent samples, each of which was analyzed in triplicate.

Whole Cell and Sandwich Hybridization Assay Intercalibration

Samples of pure culture or natural plankton populations were analyzed by filter-based whole cell hybridization and the semi-automated sandwich hybridization assay to compare the performance of both diagnostic tools. Cells labeled in the whole cell assay were quantified using epifluorescence microscopy developed above. To estimate the abundance of *P. australis* using sandwich hybridization, we applied the standard curve shown as developed above and the average reflectance value obtained from 4 PACs as noted earlier.

Whole Cell Hybridization

The protocol for identifying *P. australis* using is whole cell hybridization, as described in Example 1, relied on collecting cells by centrifugation to facilitate concentration of the sample and exchange of hybridization and wash solutions. Because cells were not recovered quantitatively after each step in the procedure, centrifugation led to variations in the estimate the abundance of *P. australis* in the original sample. Necessary manipulations of micro centrifuge tubes also made the assay labor-intensive, particularly when working with multiple samples each of which was hybridized with several probes. To overcome these problems and to speed and ease the protocol, we developed the custom filtration manifold described previously. To label target cells, samples were added to the filter stacks, concentrated by gentle vacuum filtration, and reagents added sequentially. In this manner it was possible to process multiple samples rapidly and simultaneously without centrifugation. Once the labeling and wash reactions were completed, filters were removed from the manifold and mounted on standard microscope slides to visualize labeled cells.

Tests of the filter-based labeling technique using cultured material have shown it to recover *P. australis* quantitatively. Cell abundance as estimated by counting an aliquot of culture preserved in Lugol's solution agree with estimates based on counting cells that were collected and labeled using the filter-based method. We have also applied the technique to quantify *P. australis* collected from natural populations. In this case, labeled cells are readily identified and enumerated against a background of other plankton and organic matter.

Sandwich Hybridization

As a first step to determine how the sandwich hybridization assay for *P. australis* would respond to variable numbers of target cells in natural samples, we compared a dilution series of pure culture against the same dilution series added to a concentrated net tow sample. The net tow sample contained numerous plankton species as well as other particulate matter. Nevertheless, color development for corresponding dilutions appeared equivalent. Therefore, the assay responded in proportion to the number of *P. australis* present in the sample, and was not affected by an abundance of other organisms and organic material typical of that found in nature. Results of these trials, however, relied on microtiter plate-based reactions in which beads were agitated on an orbital shaker and solutions were exchanged using a micro pipette. Although a potentially useful diagnostic, manipulations of the plates, beads and solutions were time-consuming. Moreover, results of the assay were judged visually, an attribute that made estimation of target species abundance subjective.

To speed and ease application of the sandwich hybridization assay and to facilitate quantification of color development, we incorporated the necessary solutions into reagent cassettes and fitted the *P. australis*-specific beads onto PACs. These pre-packaged reagents were applied using robotic processor as decribed by Briselden, et al., *Journal of Clinical Microbiology* 32:148–152 (1994). Trials of the sandwich hybridization assay were repeated using the semi-automated processor, and results were quantified using a reflectance scanner. The dynamic response of the assay was as observed previously; reaction intensity varied in proportion to the abundance of target cells in the sample, even when those cells occurred in a complex phytoplankton assemblage. Application of the semi-automated system also showed that the linear portion of the response curve lies between $<5 \times 10^2 - 5 \times 10^3$ cells 0.5 ml$^{-1}$ of lysate. Above this, the dynamic response is dampened.

Comparison of Whole Cell and Sandwich Hybridization Assays

Whole cell and sandwich hybridization assays were applied to net tow samples to identify and quantify naturally occurring *P. australis*. Whole cell hybridization employed the filter method, while sandwich hybridization was accomplished using the semi-automated system. Both methods tracked the relative abundance of *P. australis* equally well. However, estimates of the absolute abundance of target cells vary by a factor of 2 (on average), with sandwich hybridization yielding results that often overestimated the density of *P. australis* as compared to counts derived by filter-based whole cell hybridization. This discrepancy has not been observed when comparing the two methods using cultured cells. In the latter case, estimates of cell abundance vary by no more than 20%. It is possible that naturally occurring *P. australis* contained more rRNA per cell, on average, than those in pure culture, or that cells collected from nature were lysed more efficiently than those in culture. Either of these factors would increase the quantitative value obtained by sandwich hybridization, but neither would affect that obtained by the whole cell assay. These possibilities and others are currently under investigation. More extensive comparisons are on-going to determine whether or not this relationship is representative of the average response of the two assays.

All publications and patents mentioned in this specification are herein incorporated by reference into the specification to the same extent as if each individual publication or patent was specifically and individually indicated to be incorporated herein by reference.

What is claimed is:

1. A composition of polynucleotide probes for the detection of at least one *Pseudo-nitzschia* species from a marine sample, wherein said probes comprise a segment of nucleic acid capable of selectively hybridizing, under selective hybridizing conditions, to a hypervariable region of ribosomal RNA selected from at least one of the group consisting of:

for *P. australis*
  5'-CCGCCUGGUGGAGUGAGUCAUUU-3' (SEQ ID NO:1)
  5'-CCUGGUGGAGUGAGUCAUUU-3' (SEQ ID NO:2)
for *P. pungens*
  5'-CCGCCUGGUAAAGUGAGUCA-3' (SEQ ID NO:3)
  5'-UGGUAAAGUGAGUCAU-3' (SEQ ID NO:4)
  5'-GGCCUGGGCGCUGUGAGCUU-3' (SEQ ID NO:5)
for *P. multiseries*
  5'-CCUGGCAGAGUGAGUCAUUU-3' (SEQ ID NO:6)
  5'-UGGCAGAGUGAGUCAU-3' ( SEQ ID NO:7)
for *P. multiseries* and *P. pseudodelicatissima*
  5'-UGGCUUGGGCGCUGUGGGCU-3' (SEQ ID NO:8)
  5'-GGCUUGGGCGCUGUGGGCUU-3' (SEQ ID NO:9)
for *P. heimii*
  5'-UCUGGUAGAAUGAGUCAUGG-3' (SEQ ID NO:10)
  5'-UAUGUUCAUAUUUCCCUUG-3' (SEQ ID NO:11)
  5'-UGUGGGCGCUGUGGAUA-3' (SEQ ID NO:12)
for *P. fraudulenta*
  5'-CCUGGUAGAAUGAGUCUUU-3' (SEQ ID NO:13)
for *P. delicatissima*
  5'-UGGUAGAGUGAGUCU-3' (SEQ ID NO: 14)
for *P. americana*
  5'-UGGCUGAAUGAGUCAU-3' (SEQ ID NO:15);

with the proviso that any additional nucleic acid sequences covalently bound to said segment do not hybridize under said conditions to nucleic acids of *Pseudo-nitzschia* species in said sample.

2. A composition of claim 1 wherein said *Pseudo-nitzschia* species is *P. australis* and said hypervariable region is:
  5'-CCGCCUGGUGGAGUGAGUCAUUU-3' (SEQ ID NO:1)
  5'-CCUGGUGGAGUGAGUCAUUU-3' (SEQ ID NO:2).

3. A composition of claim 1 wherein said *Pseudo-nitzschia* species is *P. pungens* and said hypervariable region is:
  5'-CCGCCUGGUAAAGUGAGUCA-3' (SEQ ID NO:3)
  5'-UGGUAAAGUGAGUCAU-3' (SEQ ID NO:4)
  5'-GGCCUGGGCGCUGUGAGCUU-3' (SEQ ID NO:5).

4. A composition of claim 1 wherein said *Pseudo-nitzschia* species is *P. multiseries* and said hypervariable region is:
  5'-CCUGGCAGAGUGAGUCAUUU-3' (SEQ ID NO:6)
  5'-UGGCAGAGUGAGUCAU-3' (SEQ ID NO:7).

5. A composition of claim 1 wherein said *Pseudo-nitzschia* species is *P. multiseries* or *P. pseudodelicatissima* and said hypervariable region is:

5'-UGGCUUGGGCGCUGUGGGCU-3' (SEQ ID NO:8)

5'-GGCUUGGGCGCUGUGGGCUU-3' (SEQ ID NO:9).

6. A composition of claim 1 wherein said *Pseudo-nitzschia* species is *P. heimii* and said hypervariable region is:

5'-UCUGGUAGAAUGAGUCAUGG-3' (SEQ ID NO:10)

5'-UAUGUUCAUAUUUCCCUUG-3' (SEQ ID NO:11)

5'-UGUGGGCGCUGUGGAUA-3' (SEQ ID NO:12).

7. A composition of claim 1 wherein said *Pseudo-nitzschia* is *P. fraudulenta* and said hypervariable region is:

5'-CCUGGUAGAAUGAGUCUUU-3' (SEQ ID NO:13).

8. A composition of claim 1 wherein said *Pseudo-nitzschia* species is *P. delicatissima* and said hypervariable region is:

5'-UGGUAGAGUGAGUCU-3' (SEQ ID NO:14).

9. A composition of claim 1 wherein said *Pseudo-nitzschia* species is *P. americana* and said hypervariable region is:

5'-UGGCUGAAUGAGUCAU-3' (SEQ ID NO:15).

10. A polynucleotide probe for the detection of *Pseudo-nitzschia* species from a marine sample, wherein said probe comprises a segment of nucleic acid capable of selectively hybridizing, under selective hybridizing conditions, to a conserved region of ribosomal RNA, wherein said conserved region is:

5'-GATGCAAAGAACUUUGAAAAGAGAGUUAAA-GAG-3' (SEQ ID NO:16)

with the proviso that any additional nucleic acid sequences covalently bound to said segment do not hybridize under said conditions to nucleic acids of Pseudo-nitzschia species in said sample.

11. A method of detecting at least one *Pseudo-nitzschia* species from a marine sample, said method comprising the steps of:

permeabilizing the Pseudo-nitzschia to expose ribosomal RNA;

contacting said ribosomal RNA, under hybridizing conditions, with polynucleotide probes comprising a segment of nucleic acid capable of selectively hybridizing, under selective hybridizing conditions, to a hypervariable region of ribosomal RNA of said *Pseudo-nitzschia* wherein said hypervariable region is selected from at least one of the group consisting of:

for *P. australis*

5'-CCGCCUGGUGGAGUGAGUCAUUU-3' (SEQ ID NO:1)

5'-CCUGGUGGAGUGAGUCAUUU-3' (SEQ ID NO:2)

for *P. pungens*

5'-CCGCCUGGUAAAGUGAGUCA-3' (SEQ ID NO:3)

5'-UGGUAAAGUGAGUCAU-3' (SEQ ID NO:4)

5'-GGCCUGGGCGCUGUGAGCUU-3' (SEQ ID NO:5)

for *P. multiseries*

5'-CCUGGCAGAGUGAGUCAUUU-3' (SEQ ID NO:6)

5'-UGGCAGAGUGAGUCAU-3' (SEQ ID NO:7)

for *P. multiseries* and *P. pseudodelicatissima*

5'-UGGCUUGGGCGCUGUGGGCU-3' (SEQ ID NO:8)

5'-GGCUUGGGCGCUGUGGGCUU-3' (SEQ ID NO:9)

for *P. heimii*

5'-UCUGGUAGAAUGAGUCAUGG-3' (SEQ ID NO:10)

5'-UAUGUUCAUAUUUCCCUUG-3' (SEQ ID NO:11)

5'-UGUGGGCGCUGUGGAUA-3' (SEQ ID NO: 12)

for *P. fraudulenta*

5'-CCUGGUAGAAUGAGUCUUU-3' (SEQ ID NO: 13)

for *P. delicatissima*

5'-UGGUAGAGUGAGUCU-3' (SEQ ID NO:14)

for *P. americana*

5'-UGGCUGAAUGAGUCAU-3' (SEQ ID NO: 15);

and detecting hybridization complexes as an indication of the presence of *Pseudo-nitzschia* species in said sample, with the proviso that any additional nucleic acid sequences covalently bound to said segment do not hybridize under said conditions to nucleic acids of *Pseudo-nitzschia* species in said sample.

12. A method according to claim 11 wherein said *Pseudo-nitzschia* species is *P. australis* and said hypervariable region is:

5'-CCGCCUGGUGGAGUGAGUCAUUU-3' (SEQ ID NO:1)

5'-CCUGGUGGAGUGAGUCAUUU-3' (SEQ ID NO:2).

13. A method according to claim 11 wherein said *Pseudo-nitzschia* species is *P. pungens* and said hypervariable region is:

5'-CCGCCUGGUAAAGUGAGUCA-3' (SEQ ID NO:3)

5'-UGGUAAAGUGAGUCAU-3' (SEQ ID NO:4)

5'-GGCCUGGGCGCUGUGAGCUU-3' (SEQ ID NO:5).

14. A method according to claim 11 wherein said *Pseudo-nitzschia* species is *P. multiseries* and said hypervariable region is:

5'-CCUGGCAGAGUGAGUCAUUU-3' (SEQ ID NO:6)

5'-UGGCAGAGUGAGUCAU-3' (SEQ ID NO:7).

15. A method according to claim 11 wherein said *Pseudo-nitzschia* species is *P. multiseries* or *P. pseudodelicatissima* and said hypervariable region is:

5'-UGGCUUGGGCGCUGUGGGCU-3' (SEQ ID NO:8)

5'-GGCUUGGGCGCUGUGGGCUU-3' (SEQ ID NO:9).

16. A method according to claim 11 wherein said *Pseudo-nitzschia* species is *P. heimii* and said hypervariable region is:

5'-UCUGGUAGAAUGAGUCAUGG-3' (SEQ ID NO:10)

5'-UAUGUUCAUAUUUCCCUUG-3' (SEQ ID NO:11)

5'-UGUGGGCGCUGUGGAUA-3' (SEQ ID NO:12).

17. A method according to claim 11 wherein said *Pseudo-nitzschia* species is *P. fraudulenta* and said hypervariable region is:

5'-CCUGGUAGAAUGAGUCUUU-3' (SEQ ID NO:13).

18. A method according to claim 11 wherein said *Pseudo-nitzschia* species is *P. delicatissima* and said hypervariable region is:

5'-UGGUAGAGUGAGUCU-3' (SEQ ID NO:14).

19. A method according to claim 11 wherein said *Pseudo-nitzschia* is *P. americana* and said hypervariable region is:

5'-UGGCUGAAUGAGUCAU-3' (SEQ ID NO:15).

20. The method of claim 11 wherein after said *Pseudo-nitzschia* species is permeabilized, said method further comprises the step of contacting said ribosomal RNA, under hybridizing conditions, with polynucleotide probes comprising a segment of nucleic acid capable of selectively hybridizing, under selective hybridizing conditions, to a conserved region of *Pseudo-nitzschia* ribosomal RNA, wherein said conserved region is:

5'-GATGCAAAGAACUUUGAAAAGAGAGUUAAA-GAG-3' (SEQ ID NO:16), with the proviso that any additional nucleic acid sequences covalently bound to said segment do not hybridize under said conditions to nucleic acids of *Pseudo-nitzschia* species in said sample.

21. A diagnostic kit for use in determining the presence of *Pseudo-nitzschia* in a marine sample which comprises in a container a synthetic oligonucleotide probe comprising a segment of nucleic complementary to a hypervariable region of ribosomal RNA of *Pseudo-nitzschia* selected from the group consisting of:

for *P. australis*

5'-CCGCCUGGUGGAGUGAGUCAUUU-3' (SEQ ID NO:1)

5'-CCUGGUGGAGUGAGUCAUUU-3' (SEQ ID NO:2)

for *P. pungens*

5'-CCGCCUGGUAAAGUGAGUCA-3' (SEQ ID NO:3)

5'-UGGUAAAGUGAGUCAU-3' (SEQ ID NO:4)

5'-GGCCUGGGCGCUGUGAGCUU-3' (SEQ ID NO:5)

for *P. multiseries*

5'-CCUGGCAGAGUGAGUCAUUU-3' (SEQ ID NO:6)

5'-UGGCAGAGUGAGUCAU-3' (SEQ ID NO:7)

for *P. multiseries* and *P. pseudodelicatissima*

5'-UGGCUUGGGCGCUGUGGGCU-3' (SEQ ID NO:8)

5'-GGCUUGGGCGCUGUGGGCUU-3' (SEQ ID NO:9)

for *P. heimii*

5'-UCUGGUAGAAUGAGUCAUGG-3' (SEQ ID NO:10)

5'-UAUGUUCAUAUUUCCCUUG-3' (SEQ ID NO:11)

5'-UGUGGGCGCUGUGGAUA-3' (SEQ ID NO:12)

for *P. fraudulenta*

5'-CCUGGUAGAAUGAGUCUUU-3' (SEQ ID NO:13)

for *P. delicatissima*

5'-UGGUAGAGUGAGUCU-3' (SEQ ID NO:14)

for *P. americana*

5'-UGGCUGAAUGAGUCAU-3' (SEQ ID NO:15)

and combinations thereof, with the proviso that any additional nucleic acid sequences covalently bound to said segment do not hybridize under said conditions to nucleic acids of *Pseudo-nitzschia* species in said sample.

22. A diagnostic kit according to claim 21, further comprising containers having a lysing reagent, probe/enzyme reagent, wash reagent, enzyme substrate reagent, and a dipstick device.

23. A diagnostic kit according to claim 21, further comprising a synthetic oligonucleotide probe comprising a segment of nucleic complementary to a conserved region of ribosomal RNA of *Pseudo-nitzschia* wherein said conserved region is:

5'-GATGCAAAGAACUUUGAAAAGAGAGUUAAAGAG-3' (SEQ ID NO:16).

* * * * *

UNITED STATES PATENT AND TRADEMARK OFFICE
CERTIFICATE OF CORRECTION

PATENT NO.   : 5,958,689
DATED        : September 28, 1999
INVENTOR(S)  : Scholin et al.

It is certified that error appears in the above-identified patent and that said Letters Patent is hereby corrected as shown below:

Column 1,
Line 6, after the end of the sentence, the following should be inserted:
-- This invention was made with government support under grant number: NOAA NA57FDK0009 awarded by the National Oceanic and Atmospheric Administration. The government has certain rights in the invention. --

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:1:

CCGCCUGGUG GAGUGAGUCA UUU                                               23

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:2:

CCUGGUGGAG UGAGUCAUUU                                                   20

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:3:

CCGCCUGGUA AAGUGAGUCA                                                   20

(2) INFORMATION FOR SEQ ID NO:4:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:4:

UGGUAAAGUG AGUCAU                                                       16

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:5:

GGCCUGGGCG CUGUGAGCUU                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:6:

CCUGGCAGAG UGAGUCAUUU                                              20

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:7:

UGGCAGAGUG AGUCAU                                                  16

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:8:

UGGCUUGGGC GCUGUGGGCU                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:9:

GGCUUGGGCG CUGUGGGCUU                                              20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:10:

UCUGGUAGAA UGAGUCAUGG                                              20

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:11:

UAUGUUCAUA UUUCCCUUG                                                   19

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:12:

UGUGGGCGCU GUGGAUA                                                     17

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:13:

CCUGGUAGAA UGAGUCUUU                                                   19

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:14:

UGGUAGAGUG AGUCU                                                       15

(2) INFORMATION FOR SEQ ID NO:15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:15:

UGGCUGAAUG AGUCAU                                                      16

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GATGCAAAGA ACGAAAAGAG AGAAAGAG                                       28

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

AAATGACTCA CTCCACCAGG CGG                                            23

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TGACTCACTT TACCAGGCGG                                                20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AAATGACTCA CTCTGCCAGG                                                20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AGCCCACAGC GCCCAAGCCA                                                20

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
CTCTTTAACT CTCTTTTCAA AGTTCTTTGC ATC                                          33

(2) INFORMATION FOR SEQ ID NO:22:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:22:

AAATGACTCA CTCCACCAGG                                                         20

(2) INFORMATION FOR SEQ ID NO:23:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:23:

ATGACTCACT TTACCA                                                             16

(2) INFORMATION FOR SEQ ID NO:24:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:24:

AAGTCCACAG CGCCCAGGCC                                                         20

(2) INFORMATION FOR SEQ ID NO:25:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:25:

ATGACTCACT CTGCCA                                                             16

(2) INFORMATION FOR SEQ ID NO:26:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:26:

AAGCCCACAG CGCCCAAGCC                                                         20

(2) INFORMATION FOR SEQ ID NO:27:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CCATGACTCA TTCTACCAGA                                                           20

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

CAAGGGAAAT ATGAACATA                                                            19

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TATCCACAGC GCCCACA                                                              17

(2) INFORMATION FOR SEQ ID NO:30:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AAAGACTCAT TCTACCAGG                                                            19

(2) INFORMATION FOR SEQ ID NO:31:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

AGACTCACTC TACCA                                                                15

(2) INFORMATION FOR SEQ ID NO:32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

ATGACTCATT CAGCCA                                                              16

(2) INFORMATION FOR SEQ ID NO:33:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:33:

CCGCCUGGCA GAGUGAGUCA UUU                                                      23

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:34:

CCGCCUGGUA AAGUGAGUCA UU                                                       22

(2) INFORMATION FOR SEQ ID NO:35:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:35:

CCGCCUGGUA GAGUGAGUCU UU                                                       22

(2) INFORMATION FOR SEQ ID NO:36:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:36:

CCGCCUGGCU GAAUGAGUCA UUU                                                      23

(2) INFORMATION FOR SEQ ID NO:37:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: RNA (xi) SEQUENCE DESCRIPTION: SEQ ID NO:37:

```
CCGCCUGGUA GAAUGAGUCU UU                                              22

(2) INFORMATION FOR SEQ ID NO:38:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:38:

CCGUCUGGUA GAAUGAGUCA UGG                                             23

(2) INFORMATION FOR SEQ ID NO:39:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:39:

GWATTACCGC GGCKGCTG                                                   18

(2) INFORMATION FOR SEQ ID NO:40:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:40:

AGTGCAACAC TCCCACCA                                                   18

(2) INFORMATION FOR SEQ ID NO:41:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:41:

ATGACTCACT CCACCA                                                     16

(2) INFORMATION FOR SEQ ID NO:42:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:42:

TCCACAGCGC CCAGG                                                      15

(2) INFORMATION FOR SEQ ID NO:43:
```

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:43:

CCCACACGCC CAAG                                                    14

(2) INFORMATION FOR SEQ ID NO:44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

ATATCCAACC ACTGTTA                                                 17

(2) INFORMATION FOR SEQ ID NO:45:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

GCTGCCTCCC GTAGGAGT                                                18